US008236849B2

(12) United States Patent
Mahfouz et al.

(10) Patent No.: US 8,236,849 B2
(45) Date of Patent: Aug. 7, 2012

(54) MODEL FOR GLUTAMATE RACEMASE INHIBITORS AND GLUTAMATE RACEMASE ANTIBACTERIAL AGENTS

(75) Inventors: Tarek M. Mahfouz, Ada, OH (US); Kyle W. Skidmore, Springboro, OH (US); Amy Stockert, Ada, OH (US); Corey Scherer, Mentor, OH (US)

(73) Assignee: Ohio Northern University, Ada, OH (US)

( * ) Notice: Subject to any disclaimer, the term of this patent is extended or adjusted under 35 U.S.C. 154(b) by 235 days.

(21) Appl. No.: 12/580,238

(22) Filed: Oct. 15, 2009

(65) Prior Publication Data

US 2010/0240727 A1      Sep. 23, 2010

Related U.S. Application Data (60) Provisional application No. 61/105,662, filed on Oct. 15, 2008, provisional application No. 61/117,017, filed on Nov. 21, 2008, provisional application No. 61/252,135, filed on Oct. 15, 2009.

(51) Int. Cl.
  *A61K 31/405* (2006.01)
(52) U.S. Cl. .................................................... 514/415
(58) Field of Classification Search ................... 514/415
  See application file for complete search history.

(56) References Cited

U.S. PATENT DOCUMENTS

2002/0052694 A1    5/2002   McGregor et al.

(Continued)

FOREIGN PATENT DOCUMENTS

WO    WO 93/18023    9/1993

(Continued)

OTHER PUBLICATIONS

Alfonso de Dios, et al., "4-Substituted D-Glutamic Acid Analogues: The First Potent Inhibitors of Glutamate Racemase (MurI) Enzyme with Antibacterial Activity", Journal of Medicinal Chemistry, American Chemical Society, Washington, US, vol. 45, No. 20, Sep. 26, 2002, pp. 4559-4570.

Dylan Dodd, et al., "Functional Comparison of the Two *Bacillus anthracis* Glutamate Racemases", Journal of Bacteriology, vol. 189, No. 14 Jul. 2007, pp. 5265-5275.

(Continued)

*Primary Examiner* — Shengjun Wang
(74) *Attorney, Agent, or Firm* — Vorys, Sater, Seymour and Pease LLP (57) ABSTRACT

The increase in antibacterial resistance has created the demand for new antibiotics. The present invention relates to a more potent antibiotic that targets the enzyme glutamate racemase from known glutamate racemase inhibitors. Glutamate racemase catalyses the interconversion of L-glutamate to D-glutamate, making D-glutamate available, which is required for bacterial peptidoglycan biosynthesis. Knockout mutations have shown glutamate racemase to be necessary for bacterial cell survival and, before the present invention, no antibiotic on the market targeted this enzyme. The present invention relates to new, ligand based glutamate racemase inhibitors, developed using software to extract a pharmacophore model from a group of known glutamate racemase inhibitors. Forty-seven (47) known inhibitors were collected from the literature and several pharmacophore models were extracted therefrom. The functional groups common to all the known inhibitors were included in a pharmacophore model that described the requirements for glutamate racemase inhibition with 82% accuracy. Of these models, one was found to describe the requirements for glutamate racemase inhibition with 82% accuracy. The model was used to search databases of commercially available chemical compounds and 2-(2-(1H-indol-3-yl)ethylamino)-4-oxo-4-p-tolylbutanoic acid and 2-(2-(1H-indol-3-yl)ethylamino)-4-(4-fluorophenyl)-4-oxobutanoic acid were identified as showing antibacterial activity. These compounds were assayed against *S. pneumoniae* and were shown to have antibacterial activity against the non-virulent strain R6 and against a multidrug resistant strain.

5 Claims, 6 Drawing Sheets

U.S. PATENT DOCUMENTS

| | | |
|---|---|---|
| 2002/0077754 A1 | 6/2002 | McGregor et al. |
| 2004/0088118 A1 | 5/2004 | Jensen et al. |
| 2004/0152096 A1 | 8/2004 | Dietrich et al. |
| 2004/0204588 A1 | 10/2004 | DeLuca et al. |
| 2005/0009093 A1 | 1/2005 | Engkvist et al. |
| 2005/0038607 A1 | 2/2005 | Schuppert |
| 2005/0049794 A1 | 3/2005 | Van Drie et al. |
| 2005/0053978 A1 | 3/2005 | Maynard et al. |
| 2005/0136450 A1 | 6/2005 | Sutter et al. |
| 2005/0177318 A1 | 8/2005 | Young et al. |
| 2005/0266575 A1 | 12/2005 | Mayo et al. |
| 2006/0206269 A1 | 9/2006 | Diller et al. |
| 2007/0016377 A1 | 1/2007 | Ho |
| 2007/0020642 A1 | 1/2007 | Deng et al. |
| 2007/0043511 A1 | 2/2007 | Jensen et al. |
| 2007/0156343 A1 | 7/2007 | Rayan et al. |
| 2007/0198195 A1 | 8/2007 | Shaw |
| 2008/0015194 A1 | 1/2008 | Errico et al. |
| 2008/0220441 A1 | 9/2008 | Birnbaum et al. |

FOREIGN PATENT DOCUMENTS

| | | |
|---|---|---|
| WO | WO 03/068742 A1 | 8/2003 |
| WO | WO 2004/061097 | 7/2004 |
| WO | WO 2007/139946 A2 | 6/2007 |
| WO | WO 2008/057555 A2 | 5/2008 |

OTHER PUBLICATIONS

Steven L. Dixon, et al., "PHASE: a new engine for pharmacophore perception, 3D QSAR model development, and 3D database screening: 1. Methodology and preliminary results", Journal of Computer-Aided Molecular Design, Kluwer Academic Publishers, Do, vol. 20, No. 10-11, Nov. 24, 2006, pp. 647-671.

Christopher A. Lipinski, et al., "Experimental and computational approaches to estimate solubility and permeability in drug discovery and development settings", Advanced Drug Delivery Reviews, Elsevier BV, Amsterdam, NL, vol. 46, No. 1-03, Mar. 1, 2001, pp. 3-26.

Ohio Northern University, "International Search Report" PCT/US2009/060926.

2-(2-(1H-INDOL-3-YL)ETHYLAMINO)-4-OXO-4-P-TOLYLBUTANOIC ACID

FIG. 7

2-(2-(1H-INDOL-3-YL)ETHYLAMINO)-4-(4-FLUOROPHENYL)-4-OXOBUTANOIC ACID

FIG. 8

MODEL FOR GLUTAMATE RACEMASE INHIBITORS AND GLUTAMATE RACEMASE ANTIBACTERIAL AGENTS

RELATED APPLICATIONS

This application claims priority to U.S. Provisional Application No. 61/105,662, filed on Oct. 15, 2008; U.S. Provisional Application No. 61/117,017, filed on Nov. 21, 2008, and U.S. Provisional Application No. 61/252,135 filed Oct. 15, 2009, the entire disclosures of which are herein incorporated by reference.

FIELD OF THE INVENTION

The present invention relates to drug discovery and development. More specifically, the present invention relates to the development of glutamate racemase inhibitors as a class of antibiotics with enhanced pharmacokinetic properties. The invention also relates to chemical compounds with antibacterial activity against Streptococcus pneumoniae (S. pneumoniae) and a pharmacophore model that can be used to identify antibacterial drugs with good pharmacokinetic properties. The identified antibacterial compounds are inhibitors of the enzyme glutamate racemase, which is a new antibacterial target that none of the current antibiotics in the market target. This represents a new class of antibiotics that, because it has not been used before, has less resistance potential. The pharmacophore model was designed to identify compounds with less charged groups in order to improve their absorption, pharmacokinetic properties and antibacterial effectiveness.

BACKGROUND OF THE INVENTION

Antibiotic resistance is a growing problem in the world today. Antibiotic resistant strains of pathogenic bacteria emerge every day and represent a significant health care challenge According to Science, in 1980 around 1% to 5% of S. aureus was methicillin resistant and today 60% to 70% of S. aureus strains found in hospitals are methicillin resistant. This alarming increase in bacterial resistance to antibiotics has motivated an active search for novel viable targets for antibiotic drug design.

Publication Nos. US 2002/0052694 and 2002/0077754 discloses a specialized apparatus and methods for identifying, representing, and productively using high activity regions of chemical structure space. At least two representations of chemical structure space provide valuable information. A first representation has many dimensions representing members of a pharmacophore basis set and one or more additional dimensions representing defined chemical activity (e.g., pharmacological activity). A second representation has many fewer dimensions, each of which represents a principle component obtained by transforming the first representation via principal component analysis used on pharmacophore fingerprint/activity data for a collection of compounds. When the collection of compounds has the defined chemical activity, that activity will be reflected as a "high activity" region of chemical space in the second representation.

Publication No. 2005/0009093 discloses a method for generating a focused compound library containing an enriched amount of ligand compounds being capable of binding to a predetermined receptor.

Publication No. US 2005/0049794 discloses a processes for producing an optimized pharmacophore for a target protein. The invention also relates to processes for identifying compounds having an affinity to a target protein. The invention also relates to processes for designing a ligand for a target protein using the optimized pharmacophore of the present invention. The invention also provides a computer for use in designing a ligand for a target protein using the optimized pharmacophore of the present invention.

Publication No. 2005/0053978 discloses methods and systems for generating pharmacophore models characterized both by molecular features that are present in the model and features that are defined as absent. Thus, models can be developed that take into account features such as steric bulk that inhibit activity for a specified target as well as features such as functional groups that promote activity. Features that inhibit activity can be identified by comparing known active molecules with known inactive molecules. Features that are present in the inactive molecules but absent in the active molecules can be defined in a pharmacophore model.

Publication No. 2005/0177318 discloses pharmacophores in molecules identified by generating a set of conformations for a respective molecule. A respective conformation includes a series of features that are present or absent in the conformation, wherein a respective feature includes at least two molecular elements and at least one distance between the molecular elements. The features for a set of conformations for a given molecule are repeatedly compared to a model of feature importance of remaining molecules, to identify an inferred conformation of a given molecule, until the model of feature importance for the molecules converges.

Publication No. US 2006/0206269 discloses a set of molecules, the members of which have the same type of biological activity, represented as one-dimensional strings of atoms. The one-dimensional strings of all members of the set are aligned, in order to obtain a multiple alignment profile of a consensus active compound. The one-dimensional multiple alignment profile is used in deriving a one-dimensional QSAR model to identify other compounds likely to have the same biological activity, and also may be used to derive a three-dimensional multiple alignment profile of the molecules in the set.

Publication No. US 2007/0156343 discloses a stochastic algorithm for predicting the drug-likeness of molecules. It is based on optimization of ranges for a set of descriptors. Lipinski's "rule-of-5", which takes into account molecular weight, log P, and the number of hydrogen bond donor and acceptor groups for determining bioavailability, was previously unable to distinguish between drugs and non-drugs with its original set of ranges. The invention demonstrates the predictive power of the stochastic approach to differentiate between drugs and non-drugs using only the same four descriptors of Lipinski, but modifying their ranges. However, there are better sets of 4 descriptors to differentiate between drugs and non-drugs, as many other sets of descriptors were obtained by the stochastic algorithm with more predictive power to differentiate between databases (drugs and non-drugs). A set of optimized ranges constitutes a "filter". In addition to the "best" filter, additional filters (composed of different sets of descriptors) are used that allow a new definition of "drug-like" character by combining them into a "drug like index" or DLI. In addition to producing a DLI (drug-like index), which permits discrimination between populations of drug-like and non-drug-like molecules, the present invention may be extended to be combined with other known drug screening or optimizing methods, including but not limited to, high-throughput screening, combinatorial chemistry, scaffold prioritization and docking.

Publication No. US 2007/0198195 discloses a computational method of determining a set of proposed pharmacophore features describing interactions between a known biological target and known training ligands that show activity towards the biological target.

The identification of potentially novel drugs and molecular targets can assist in preventing antibiotic resistance. Bacterial peptidoglycan biosynthesis is a well validated and a very attractive target for the design and discovery of new antibacterial agents since it is unique to bacteria cells (does not occur in humans) and are unexploited steps in the pathway. Currently, several bactericidal antibiotics available on the market target the bacterial peptidoglycan biosynthesis pathway, e.g., vancomycin. However, these agents are highly susceptible to resistance.

A new drug target in the peptidoglycan biosynthetic pathway is glutamate racemase (glu racemase), an enzyme which catalyses the conversion of L-glutamate to D-glutamate providing D-glutamate for peptidoglycan biosynthesis. Knockout mutations have shown the glutamate racemase gene to be essential in *Escherichia coli* (*E. coli*) and *S. pneumoniae*. Recently, a group of glutamate racemase inhibitors were developed[1] through chemical synthesis but enthusiasm for these agents waned as they possessed a narrow spectrum of antibacterial activity against only *S. pneumoniae*. The apparent poor antibacterial activity of these compounds was due in part to poor membrane permeability.

[1] de Dios A, Prieto L, Martin J A, et al. 4-substituted D-glutamic acid analogues: The first potent inhibitors of glutamate racemase (MurI) enzyme with antibacterial activity. J Med. Chem. 2002; 45:4559-4570

Therefore, a drawback of known glutamate racemase inhibitors is their poor lipophilic nature. It was hypothesized that the charged groups in the D-glu-analogue inhibitors[2] make them poorly lipophilic and unable to permeate through biological membranes. The minimum inhibitory concentration (MIC) from whole-cell assays of some of these inhibitors did not correlate with their $IC_{50}$ values from the in vitro enzyme assays further supporting this hypothesis. In addition, the poor lipophilic nature of these inhibitors makes them poor drug candidates as they will show poor gut permeability and poor absorption from the intestine.

[2] Id.

Accordingly, there remains a need for glutamate racemase inhibitors with enhanced lipophilic properties. Eliminating some or all of the charged groups enhances the lipophilic nature of these inhibitors and, as a consequence, enhances their membrane permeability properties which in turn enhances not only their antibacterial spectrum but their pharmacokinetic profile as well. However, those charged groups may be essential for binding and inhibition of the enzyme. The present invention is directed to a method of enhancing the pharmacokinetic profile of the charged poorly lipophilic glu racemase inhibitors while preserving their antibacterial activity using a ligand-based drug design approach.

SUMMARY OF THE INVENTION

One of the unexploited steps in bacterial peptidoglycan biosynthesis is the step catalyzed by the enzyme glutamate racemase. This enzyme catalyses the conversion of L-glutamate to D-glutamate which is a necessary component in the formation of bacterial peptidoglycan. Knockout mutations in *S. pneumoniae* have shown glutamate racemase to be essential for the viability of this bacterium. Thus, glutamate racemase inhibitors represent a new class of antibiotics with less resistance potential.

The present invention relates to pharmacophore model ADNRR2584, a computational model that can be used to identify new potent glutamate racemase inhibitors with antibacterial activity and enhanced absorption properties, including membrane permeability, through virtual screening of databases of commercially available chemical compounds. The model of the present invention saves time and greatly reduces the expenses in the drug development process because it can predict the activity of commercially available compounds precluding the need for chemical synthesis.

It is an object of the present invention to inhibit bacterial growth.

It is another object of the present invention to identify new antibacterial agents with less resistance potential and with enhanced pharmacokinetic properties.

It is another object of the present invention to speed up the process of antibacterial discovery and reduce the associated cost.

It is another object of the present invention to provide a model that assigns a predicted activity to the compounds it identifies.

It is a further object of the present invention to provide a pharmacophore model for glutamate racemase inhibitors that will facilitate the identification of new glutamate racemase inhibitors with antibacterial activities.

It is a further object of the present invention to provide a pharmacophore model that can be used to screen a large number of compounds in silico to identify new antibacterial agents and predict their activities.

It is a further object of the present invention to provide a pharmacophore model with no more than one charged element to identify compounds with enhanced pharmacokinetic properties.

It is a further object of the present invention to provide a pharmacophore model that is modified to identify compounds with enhanced pharmacokinetic properties.

It is a further object of the present invention to provide an accurate QSAR model associated with the pharmacophore model that can predict the activity of any identified compound with 82% accuracy.

It is a further object of the present invention to identify compounds that demonstrate antibacterial activity against multidrug resistant *S. pneumoniae* when tested in whole cell assays.

It is yet a further object of the present invention to provide a method of identifying antibacterial agents with enhanced pharmacokinetic properties comprising the steps of a) developing pharmacophore models based on known glutamate racemase inhibitors; b) excluding models with more than one charged element to obtain remaining models with enhanced pharmacokinetic properties; and c) identifying compounds by searching chemical databases for compounds comprising a structure closest to the remaining models.

It is yet a further object of the present invention to provide a method of identifying antibacterial agents with enhanced pharmacokinetic properties comprising the steps of a) developing pharmacophore models based on known glutamate racemase inhibitors; b) modifying elements in the pharmacophore models to enhance pharmacokinetic properties of the models and obtain modified models; and c) identifying compounds by searching chemical databases for compounds comprising a structure closest to the modified models.

Figure 4:
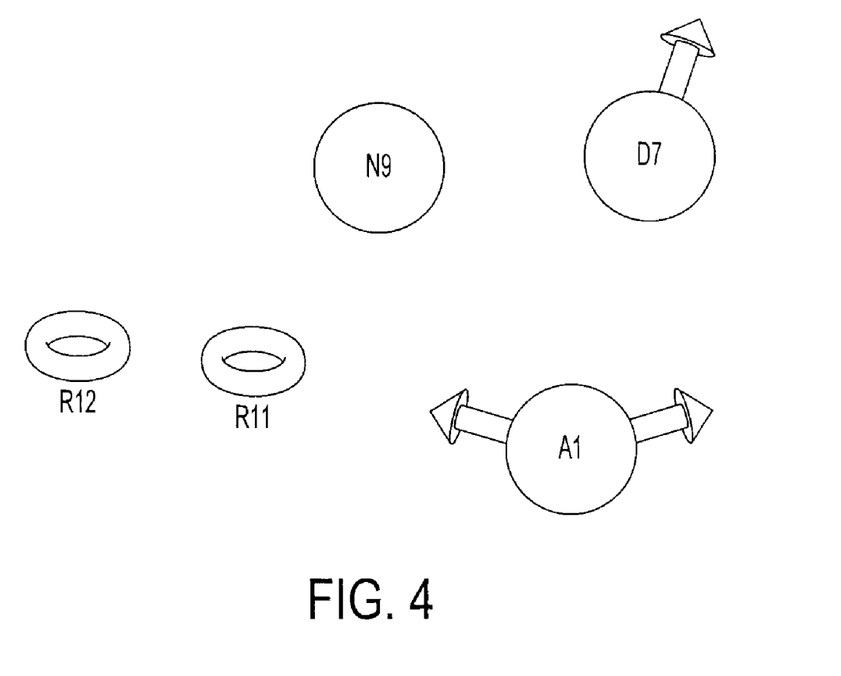
FIG. 4 is a schematic representation of the pharmacophore model of the present invention.

It is yet a further object of the present invention to provide a pharmacophore model comprising the structure shown in FIG. 4, wherein N9 represents a negative ionizable site, D7 a hydrogen bond donor site, A1 a hydrogen bond acceptor site and both R11 and R12 are aromatic ring sites.

Figure 6:
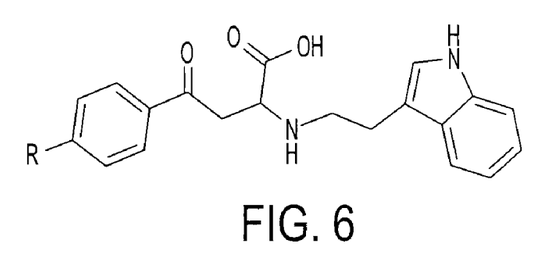
FIG. 6 shows the general structure of the compound of the present invention.

It is yet a further object of the present invention to provide a method of treating a *S. pneumoniae* infection comprising administering to a mammal in need of treatment, an effective amount of a compound comprising the structure shown in FIG. 6, wherein R comprises —CH3, —F, —Cl, or —Br.

It is yet a further object of the present invention to provide a method of treating a *S. pneumoniae* infection comprising administering to a mammal in need of treatment, an effective amount of 4-(4-fluorophenyl)-2-{[2-(1H-indol-3-yl)ethyl]amino}-4-oxobutanoic acid, 2-(2-(1H-indol-3-yl)ethylamino)-4-oxo-4-p-tolylbutanoic acid, 2-(2-(1H-indol-3-yl)ethylamino)-4-(4-chlorophenyl)-4-oxobutanoic acid, 2-(2-(1H-indol-3-yl)ethylamino)-4-(4-bromophenyl)-4-oxobutanoic acid, or a combination thereof.

There has thus been outlined, rather broadly, the more important features of the invention in order that the detailed description thereof that follows may be better understood, and in order that the present contribution to the art may be better appreciated. There are, of course, additional features of the invention that will be described further hereinafter.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception upon which this disclosure is based may be readily utilized as a basis for the designing of other structures, methods and systems for carrying out the several purposes of the present invention. It is important, therefore, that equivalent constructions insofar as they do not depart from the spirit and scope of the present invention, are included in the present invention.

For a better understanding of the invention, its operating advantages and the aims attained by its uses, reference should be made to the accompanying drawings and descriptive matter which illustrate preferred embodiments of the invention.

DETAILED DESCRIPTION OF THE PREFERRED EMBODIMENTS

Figure 1:
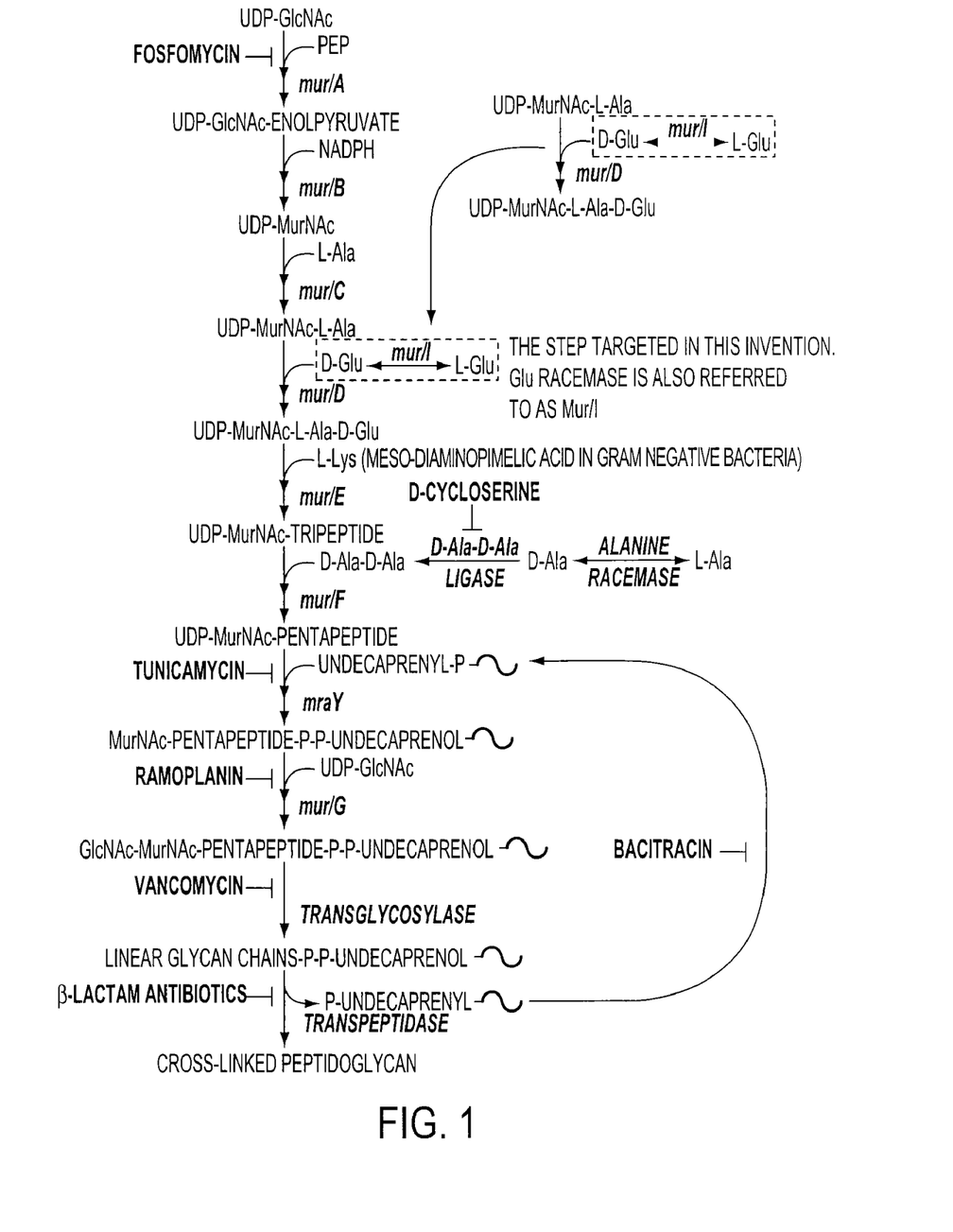
FIG. 1 is a schematic representation of the bacterial peptidoglycan biosynthetic pathway showing known antibiotic targets.

FIG. 1 is a schematic representation of the bacterial peptidoglycan biosynthetic pathway showing known antibiotic targets. D-glutamate is required for the synthesis of the cell wall. The enzyme glutamate racemase (also known as MurI) is the enzyme that converts L-glutamate to the necessary D-glutamate for bacterial cell survival.

Figure 2:
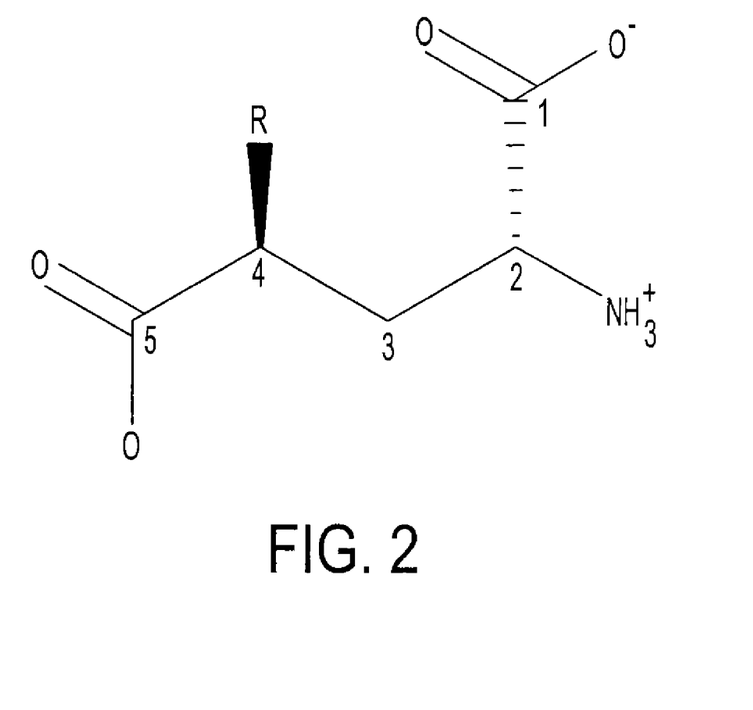
FIG. 2 shows the general structure of glutamate racemase inhibitors.

Because there is no structure available for glutamate racemase from *S. pneumoniae*, ligand-based drug design approaches can be used to develop potent glutamate racemase inhibitors. Known glutamate racemase inhibitors[3] were not as effective as desired. They were highly charged compounds and, therefore, were expected to have poor membrane permeability. FIG. 2 shows the general structure of glutamate racemase inhibitors. All inhibitors were derivatives of D-glutamic acid, which explains the highly charged nature of these inhibitors. R is an aliphatic or an aromatic hydrophobic group. They showed antibacterial activity against only *S. pneumonia*, which could have been due to their poor membrane permeability. Calculations of the absorption, distribution, metabolism and excretion (ADME) properties of these inhibitors strongly support this hypothesis (see Table 3) especially, the oil/water partition coefficient (Po/w) values which can be used as an indicator of membrane permeability. Another possible reason for the narrow scope of antibacterial activity could be the low similarity among glutamate racemases from different organisms.

[3] Id.

To develop potent glutamate racemase inhibitors with improved lipid solubility and, hence, better antibacterial spectrum, the method of the present invention involves extracting a pharmacophore model from a group of known glutamate racemase inhibitors and modifying it so that the functional groups required for glutamate racemase inhibition are preserved while enhancing lipid solubility.

Commercially available software (Schrödinger's PHASE) was used for pharmacophore modeling and database screening. The overall protocol for identifying new glutamate racemase inhibitors with improved pharmacokinetic properties involves:

1. Developing a pharmacophore model for glutamate racemase inhibitors from a group of already known inhibitors with poor pharmacokinetic properties.

2. Modify the elements in the pharmacophore model to enhance the pharmacokinetic properties of potential inhibitors.

3. Developing a Quantitative Structure-Activity Relationship (QSAR) model that can predict glutamate racemase inhibition activity for unknown compounds with reasonable accuracy.

4. Searching several databases of commercially available chemical compounds with the developed pharmacophore model to identify new potential inhibitors.

5. In silico calculation of pharmacokinetic properties of the identified compounds.

6. Screening the identified compounds and selecting only those with enhanced potency and pharmacokinetic properties for antibacterial activity testing.

More specifically, the methods involve the following:
Developing the Pharmacophore Model:

Database Searching and Compound Selection:

The method of developing the pharmacophore model comprises the steps of a) identifying known glutamate racemase inhibitors with biological activity and poor pharmacokinetic properties; b) identifying elements common to all the known glutamate racemase inhibitors; and c) developing models that contain about 3-6 common elements, preferably 5 elements. According to a preferred embodiment, the biological activity comprises antibacterial activity, more preferably, the biological activity is experimentally determined based on at least one of IC50, Ki, MIC value and any other experimental measures of biological activity.

The method further comprises the steps of a) developing a quantitative structure-activity relationship (QSAR) model; b) selecting a QSAR model with the highest ($R^2$) value; and c) identifying compounds by searching chemical databases for compounds comprising a structure closest to the selected model. According to a preferred embodiment, the QSAR model predicts at least one of the $IC_{50}$, Ki, MIC value and any other measure of biological activity of the compounds with an accuracy of at least about 70%, preferably 80%, more preferably 90%. According to a further preferred embodiment, the method further comprises the step of calculating the $IC_{50}$ value of the identified compounds.

The step of developing the QSAR model comprises the steps of a) identifying known glutamate racemase inhibitors with poor pharmacokinetic properties; b) classifying the known inhibitors into groups depending on their biological activity; c) creating a training set comprising about 25 inhibitors, wherein the training set comprises at least one known inhibitor from each group; d) creating a test set comprising the remaining known inhibitors; e) developing the QSAR model based on the training set; f) using the QSAR model to calculate at least one of the $IC_{50}$, Ki, MIC value and any other measure of biological activity of the test set; and g) calculating the $R^2$ value by comparing the calculated $IC_{50}$, Ki, MIC value and any other measure of biological activity of the test set with the known $IC_{50}$, Ki, MIC value and any other measure of biological activity of the test set. According to a preferred embodiment, the step of classifying the known inhibitors by their biological activity comprises classifying the known inhibitors as highly active if they have an $IC_{50}$ value of less than 0.07, moderately active if they have an $IC_{50}$ value of 0.07-0.8, active if they have an $IC_{50}$ value of 0.8-10, slightly active if they have an $IC_{50}$ value of 10-100, and weakly active if they have an $IC_{50}$ of above 100.

Whole-cell Assays: Selected compounds were assayed against *S. pneumoniae* on blood agar plates as shown on FIG. 3.

Table 1 shows the results of six pharmacophore models extracted from the 47 known glutamate racemase inhibitors[5]. The $R^2$ value delineates how accurate a model is in predicting an inhibitor's $IC_{50}$. Model 6 had the highest $R^2$ value.

[5] Id.

TABLE 1

| Model Number | $R^2$ Value |
| --- | --- |
| 1 | 0.20 |
| 2 | 0.58 |
| 3 | 0.80 |
| 4 | 0.76 |
| 5 | 0.77 |
| 6 | 0.82 |

FIG. 4 is a schematic representation of Model 6 (AD-NRR2584), the pharmacophore model of the present invention. The pharmacophore model, Model 6, contains five sites as shown seen in FIG. 4: site A1 (sphere with 2 arrows) represents a hydrogen bond acceptor functional group, site N9 (sphere with no arrow) represents a negative ionizable functional group), site D7 (sphere with 1 arrow) represents a hydrogen bond donor functional group), and both sites R11 and R12 (small rings) represent an aromatic ring. Distances and angles between the sites are shown in Tables 2 and 3, respectively. According to a preferred embodiment, only one charged center (N9) is maintained in the model. The other two charged centers are replaced by neutral groups to enhance the lipophilicity of identified compounds, i.e., the negatively charged elements in the model are replaced with hydrogen-bond acceptor groups and the positively charged elements in the model are replaced with hydrogen-bond donor groups.

TABLE 2

Model 6 (ADNRR2584) inter-site distances.

| Site 1 | Site 2 | Distance in Å |
|---|---|---|
| A1 | D7 | 4.398 |
| A1 | N9 | 5.034 |
| A1 | R11 | 5.847 |
| A1 | R12 | 7.940 |
| D7 | N9 | 3.376 |
| D7 | R11 | 7.186 |
| D7 | R12 | 9.163 |
| N9 | R11 | 4.436 |
| N9 | R12 | 6.165 |
| R11 | R12 | 2.136 |

TABLE 3

Model 6 (ADNRR2584) inter-site angles.

| Site 1 | Site 2 | Site 3 | Angle in degrees |
|---|---|---|---|
| D7 | A1 | N9 | 41.3 |
| D7 | A1 | R11 | 87.9 |
| D7 | A1 | R12 | 91.3 |
| N9 | A1 | R11 | 47.4 |
| N9 | A1 | R12 | 50.9 |
| R11 | A1 | R12 | 3.6 |
| A1 | D7 | N9 | 79.5 |
| A1 | D7 | R11 | 54.4 |
| A1 | D7 | R12 | 60.0 |
| N9 | D7 | R11 | 26.7 |
| N9 | D7 | R12 | 22.1 |
| R11 | D7 | R12 | 5.7 |
| A1 | N9 | D7 | 59.2 |
| A1 | N9 | R11 | 76.0 |
| A1 | N9 | R12 | 89.7 |
| D7 | N9 | R11 | 133.3 |
| D7 | N9 | R12 | 146.1 |
| R11 | N9 | R12 | 13.8 |
| A1 | R11 | D7 | 37.7 |
| A1 | R11 | N9 | 56.6 |
| A1 | R11 | R12 | 166.5 |
| D7 | R11 | N9 | 20.0 |
| D7 | R11 | R12 | 154.7 |
| N9 | R11 | R12 | 136.6 |
| A1 | R12 | D7 | 28.7 |
| A1 | R12 | N9 | 39.3 |
| A1 | R12 | R11 | 9.9 |
| D7 | R12 | N9 | 11.9 |
| D7 | R12 | R11 | 19.6 |
| N9 | R12 | R11 | 29.6 |

Figure 5:
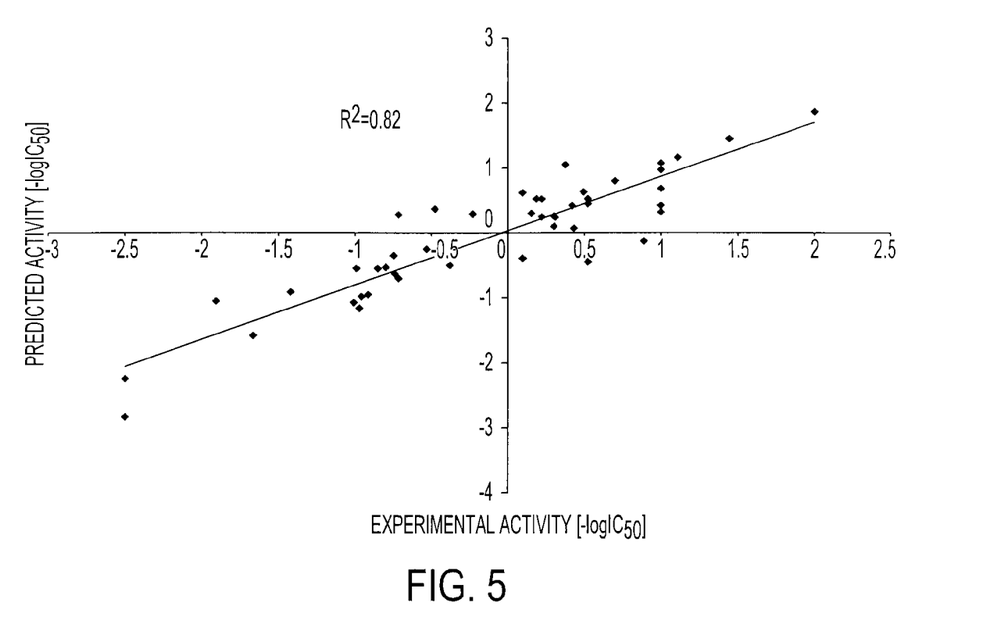
FIG. 5 is a plot showing the correlation between experimental activity of the known glutamate racemase inhibitors and their calculated activity using the pharmacophore model of the present invention.

FIG. 5 shows the correlation between experimental activity of the known glutamate racemase inhibitors and their calculated activity using Model 6. The $R^2$ plot for Model 6 shows how well the predicted $IC_{50}$ values agree with their corresponding experimental values.

Table 4 shows 17 compounds identified by Model 6 as potential glutamate racemase inhibitors. Compounds A and B had the lowest $IC_{50}$, i.e., highest activity, and therefore, their ADME properties were calculated and these compounds were selected for bacterial assays.

TABLE 4

| Entry ID | Title | No. Sites Matched | Fitness | Predicted $IC_{50}$ mg/mL |
|---|---|---|---|---|
| 1 | ligand_7567 | 5 | 1.4 | 6.3 |
| 2 | ligand_31939 | 5 | 1.3 | 1.1 |
| 3 | ligand_49854 | 5 | 1.2 | 6.4 |
| 4 | ligand_48140 | 5 | 1.2 | 0.65 |
| 5 | ligand_26895 | 5 | 1.1 | 13.8 |
| 6 | ligand_48139 | 5 | 1.1 | 1.1 |

TABLE 4-continued

| Entry ID | Title | No. Sites Matched | Fitness | Predicted $IC_{50}$ mg/mL |
|---|---|---|---|---|
| 7 | ligand_48150 | 5 | 1.1 | 1.8 |
| 8 | ligand_39818 | 5 | 1 | 1.7 |
| A | ligand_48151 | 5 | 0.9 | 0.45 |
| B | ligand_48287 | 5 | 0.9 | 0.49 |
| 11 | ligand_48136 | 5 | 0.8 | 1.1 |
| 12 | ligand_32329 | 5 | 0.8 | 1.3 |
| 13 | ligand_48147 | 5 | 0.8 | 1.7 |
| 14 | ligand_26896 | 5 | 0.7 | 2.6 |
| 15 | ligand_48148 | 5 | 0.5 | 1.2 |
| 16 | ligand_48286 | 5 | 0.5 | 2.2 |
| 17 | ligand_48137 | 5 | 0.1 | 1.1 |

Table 5 shows the relevant ADME properties as calculated by QikProp for the known compounds[6] and compounds A and B above. The calculated ADME properties are: $P_{O/W}$ which is an indicator of the lipophilicity of the compound (low values represent poor lipid solubility), S which is the aqueous solubility, and Caco-2 which is an indicator of the human gut permeability. Ranges in parentheses represent ranges for 90% of drugs in the market today.

[6] Id.

TABLE 5

| Compound | Log $P_{O/W}$ (−2.0 to 6.5) | Log $S^b$ (−6.5 to 0.5) | Caco-2 nm/sec (<25 poor and >500 great) |
|---|---|---|---|
| Known compounds | | | |
| 24 | 0.53 | −2.886 | 1 |
| 60 | −0.835 | −2.128 | 0 |
| 69 | −0.193 | −2.042 | 1 |
| 74 | 0.142 | −2.493 | 1 |
| Compounds of the present invention | | | |
| A | 2.0 | −5.0 | 18.9 |
| B | 1.9 | −4.7 | 18.9 |

For the known compounds in Table 5, the structure is as shown in FIG. 2, with the R as listed below in Table 6:

TABLE 6

| Known Compound | R Group |
|---|---|
| 24 |  |
| 60 |  |
| 69 |  |
| 74 |  |

Figure 3:
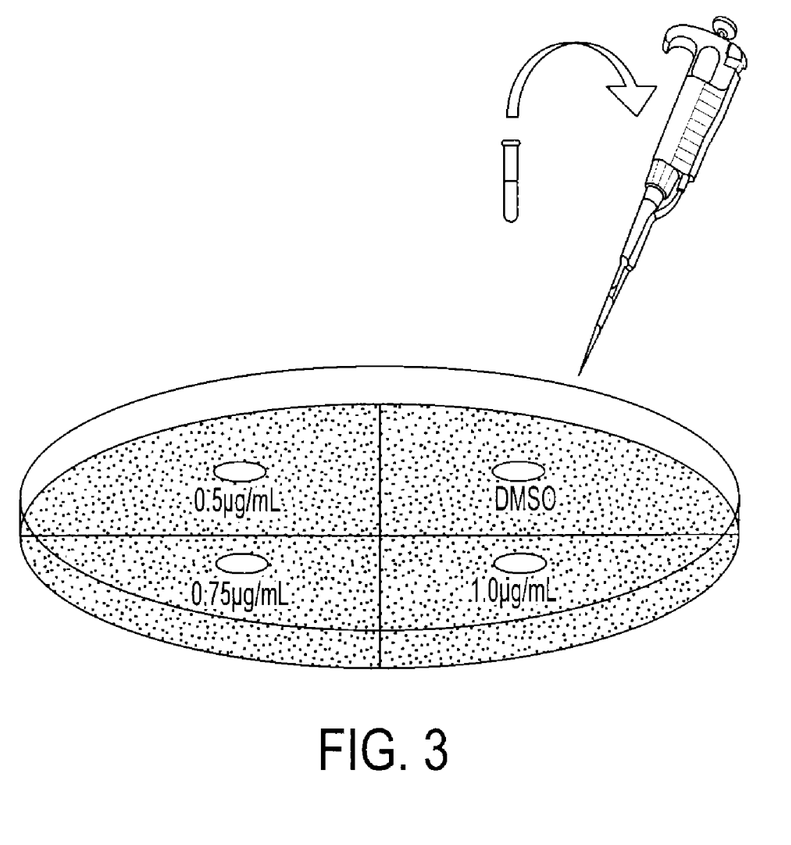
FIG. 3 is a schematic representation of the whole cell assay used to verify antibacterial activity against multidrug resistant *S. pneumoniae*.

The antibacterial activity of Compound B against *S. pneumoniae* R6 strain was assayed as shown in FIG. 3. Compound B was tested at three different concentrations, 0.5 µg/mL, 0.75 µg/mL, and 1.0 µg/mL as shown in FIG. 3 and inhibition zones were compared to that around DMSO, which is the solvent used to dissolve Compound B. Compound B showed significant antibacterial activity as compared to the DMSO (data not shown). Compound A was also tested but showed weaker antibacterial activity than Compound B (data not shown).

Figure 7:
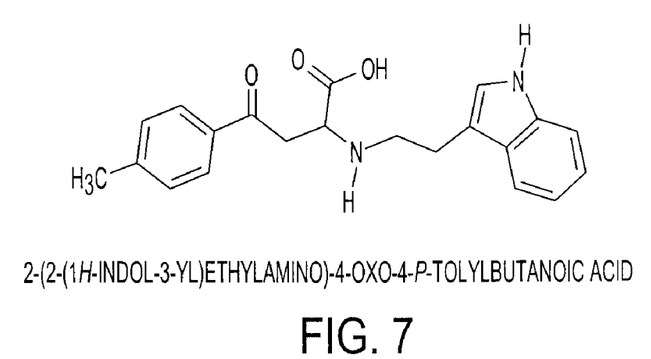
FIG. 7 shows the chemical structure of 2-(2-(1H-indol-3-yl)ethylamino)-4-oxo-4-p-tolylbutanoic acid.
Figure 8:
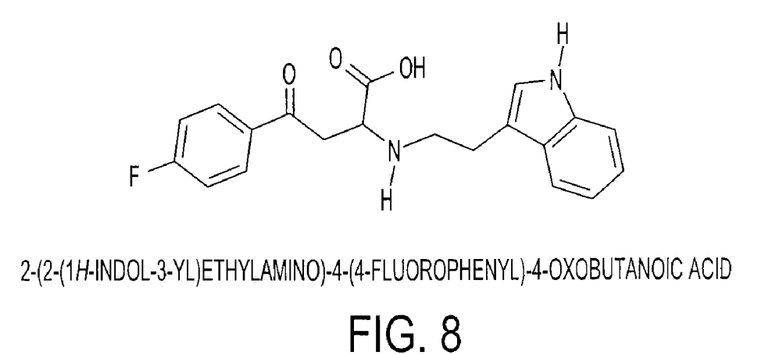
FIG. 8 shows the chemical structure of 2-(2-(1H-indol-3-yl)ethylamino)-4-(4-fluorophenyl)-4-oxobutanoic acid.

FIG. 6 shows the general structure of the compound identified by Model 6 (ADNRR2584), wherein R comprises —CH3, —F, —Cl, or —Br. The structure of Compound A is shown in FIG. 7, which shows 2-(2-(1H-indol-3-yl)ethylamino)-4-oxo-4-p-tolylbutanoic acid, and the structure of Compound B is shown in FIG. 8, which shows 2-(2-(1H-indol-3-yl)ethylamino)-4-(4-fluorophenyl)-4-oxobutanoic acid. The protocol for identifying new antibacterial agents using Model 6 (ADNRR2584) involves searching databases of commercially available chemical compounds with the model using the appropriate computer program to identify new potential inhibitors. The compounds 2-(2-(1H-indol-3-yl)ethylamino)-4-(4-chlorophenyl)-4-oxobutanoic acid and 2-(2-(1H-indol-3-yl)ethylamino)-4-(4-bromophenyl)-4-oxobutanoic acid were also identified in this fashion.

Through ligand-based drug design approach, a pharmacophore model that can identify glutamate racemase inhibitors with antibacterial activity with 82% success rate can be identified. The present invention shows that through modifications of pharmacophore sites, the ADME properties of the identified compounds can be controlled.

The present invention contemplates using Model 6 to search more and larger chemical compound databases to identify compounds with even better antibacterial activities and better membrane permeabilities. The present invention also contemplates determining the antibacterial spectrum of the identified compounds by testing them against different strains of bacteria. The present invention further contemplates mixing together these results and the results from structure-based drug design approaches to develop glutamate racemase with broader spectrum of antibacterial activity.

Having now described a few embodiments of the invention, it should be apparent to those skilled in the art that the foregoing is merely illustrative and not limiting, having been presented by way of example only. Numerous modifications and other embodiments are within the scope of the invention and any equivalent thereto. It can be appreciated that variations to the present invention would be readily apparent to those skilled in the art, and the present invention is intended to include those alternatives.

Further, since numerous modifications will readily occur to those skilled in the art, it is not desired to limit the invention to the exact construction and operation illustrated and described, and accordingly, all suitable modifications and equivalents may be resorted to as falling within the scope of the invention.

The invention claimed is:

1. A method of treating a *Streptococcus pneumoniae* infection comprising administering to a mammal in need of treatment, an effective amount of a compound comprising the structure wherein R comprises —CH3, —F, —Cl, and —Br.

2. The method of claim 1, wherein the compound comprises 2-(2-(1H-indol-3-yl)ethylamino)-4-(4-fluorophenyl)-4-oxobutanoic acid.

3. The method of claim 1, wherein the compound comprises 2-(2-(1H-indol-3-yl)ethylamino)-4-oxo-4-p-tolylbutanoic acid.

4. The method of claim 1, wherein the compound comprises 2-(2-(1H-indol-3-yl)ethylamino)-4-(4-chlorophenyl)-4-oxobutanoic acid.

5. The method of claim 1, wherein the compound comprises 2-(2-(1H-indol-3-yl)ethylamino)-4-(4-bromophenyl)-4-oxobutanoic acid.

* * * * *